United States Patent [19]
Johnson et al.

[11] Patent Number: 5,695,513
[45] Date of Patent: Dec. 9, 1997

[54] FLEXIBLE CUTTING TOOL AND METHODS FOR ITS USE

[75] Inventors: Wesley D. Johnson, Chanhassen; Gregg S. Sutton, Plymouth, both of Minn.; Bruce Wayne Stursa, Hudson; Francis C. Peterson, Prescott, both of Wis.

[73] Assignee: Metagen, LLC, Menomonie, Wis.

[21] Appl. No.: 609,363

[22] Filed: Mar. 1, 1996

[51] Int. Cl.[6] ............................................. A61B 17/32
[52] U.S. Cl. ...................................... 606/180; 606/167
[58] Field of Search ................................. 606/180, 167, 606/166, 169-170, 171, 173; 128/751-752; 408/1, 713, 122; 30/205-206, 216, 240; 433/131-132

[56] References Cited

U.S. PATENT DOCUMENTS

| | | |
|---|---|---|
| 4,867,155 | 9/1989 | Isaacson . |
| 4,998,527 | 3/1991 | Meyer . |
| 5,320,635 | 6/1994 | Smith ........................ 606/180 |
| 5,322,505 | 6/1994 | Krause et al. ................ 606/180 |
| 5,376,100 | 12/1994 | Lefebvre ...................... 606/180 |

*Primary Examiner*—Michael Buiz
*Assistant Examiner*—Nancy Connolly Mulcare
*Attorney, Agent, or Firm*—Fredrikson & Byron, PA

[57] ABSTRACT

A cable comprising helically wound superelastic fibers and having a drilling tip provided at its distal end is housed in an elongated holder through which the cable may be advanced, the holder having a distal end for supporting the cable during a drilling operation and through which the distal end of the cable may protrude. The holder includes contains a cable support shaped to bend the cable through a predetermined angle adjacent its distal end and to support the cable as it is rotated and advanced. A motor is attached to the cable remote from the distal end of the cable to rotate the cable in a direction tending to tighten the cable fibers.

4 Claims, 8 Drawing Sheets

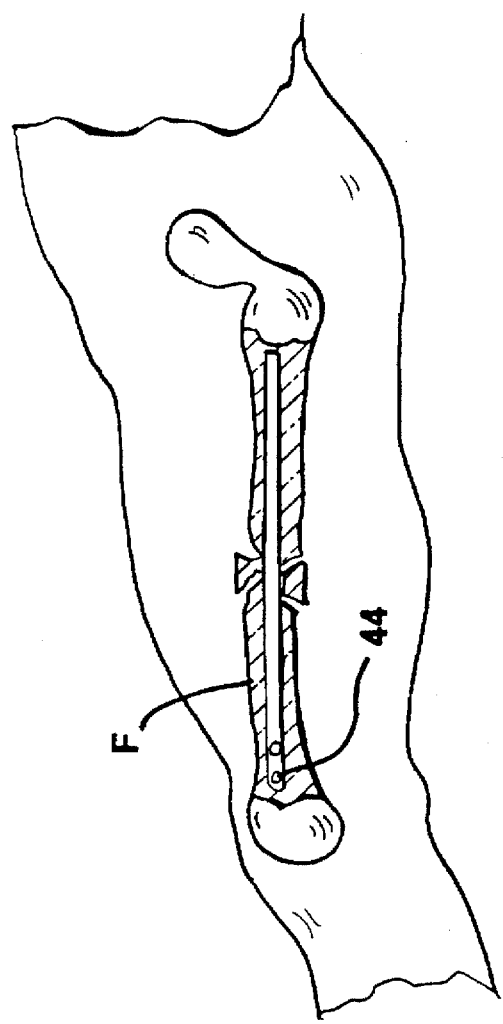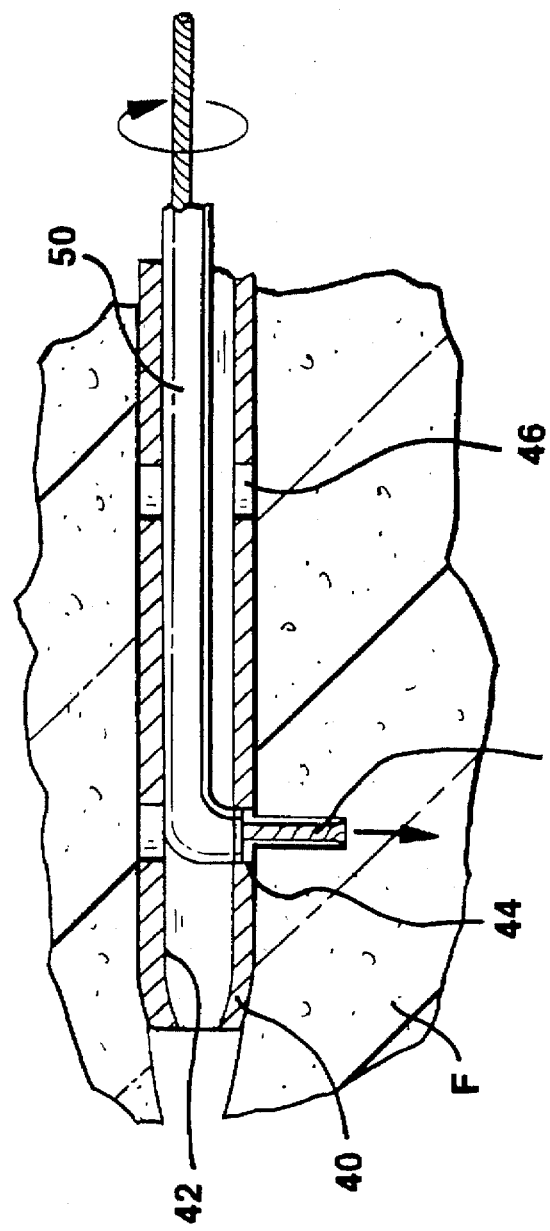

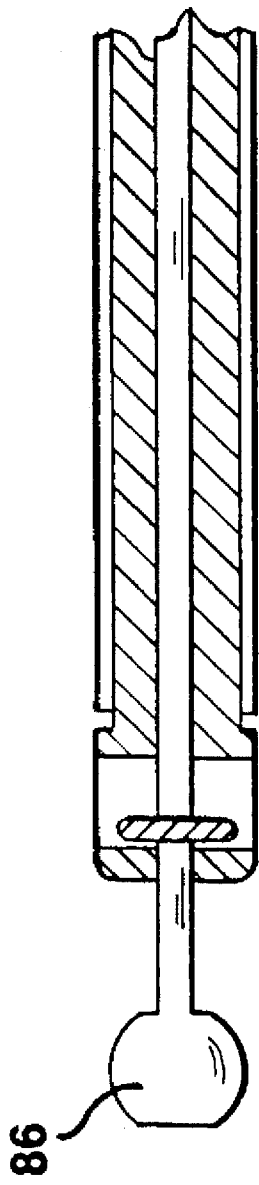
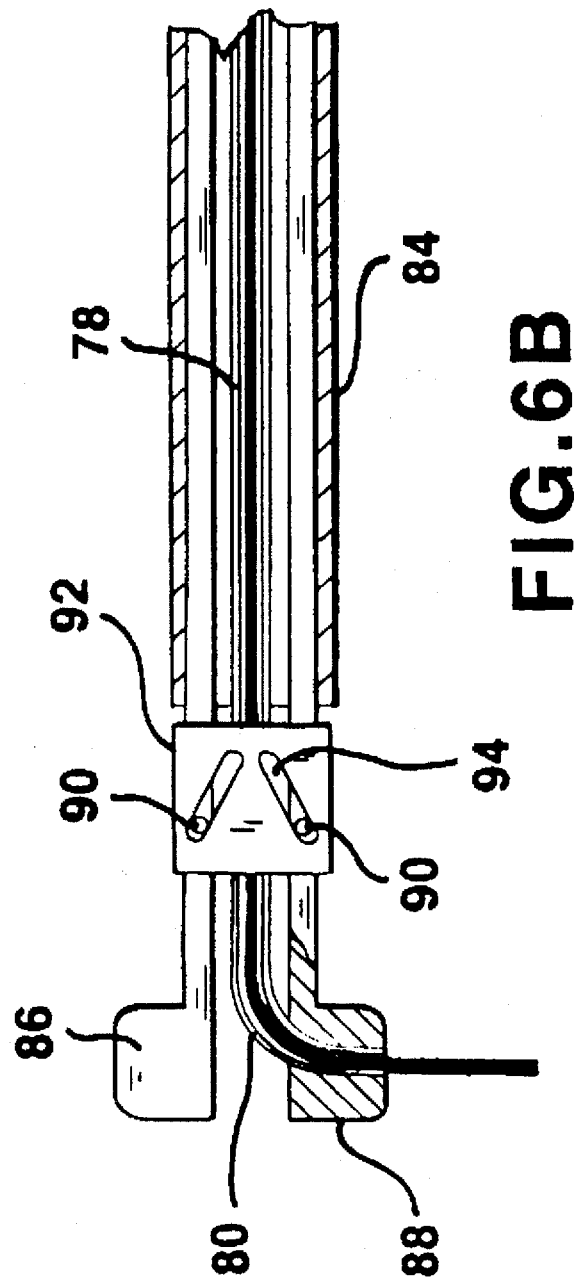
FIG.6A
FIG.6B

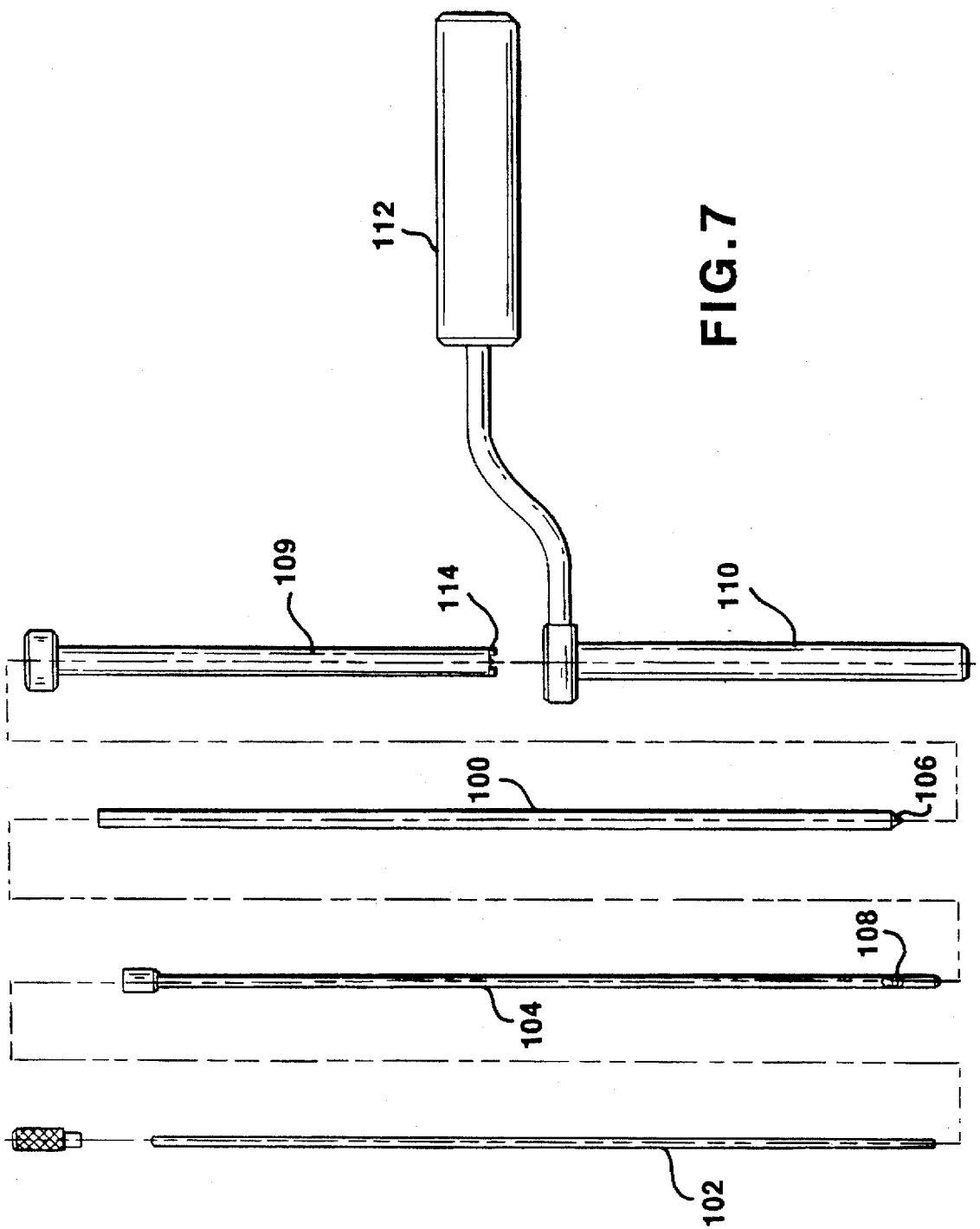

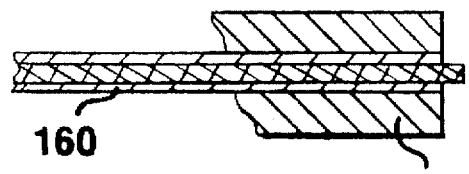
FIG.10A
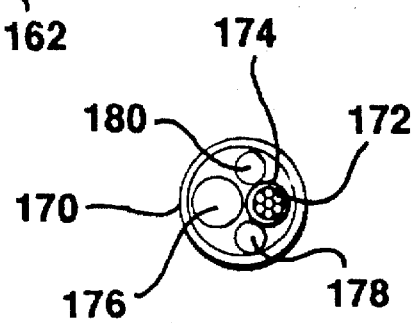
FIG.11
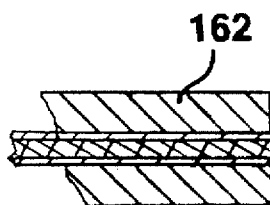
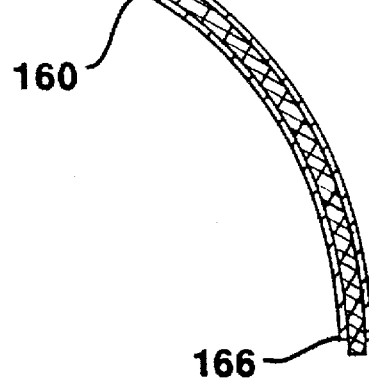
FIG.10B
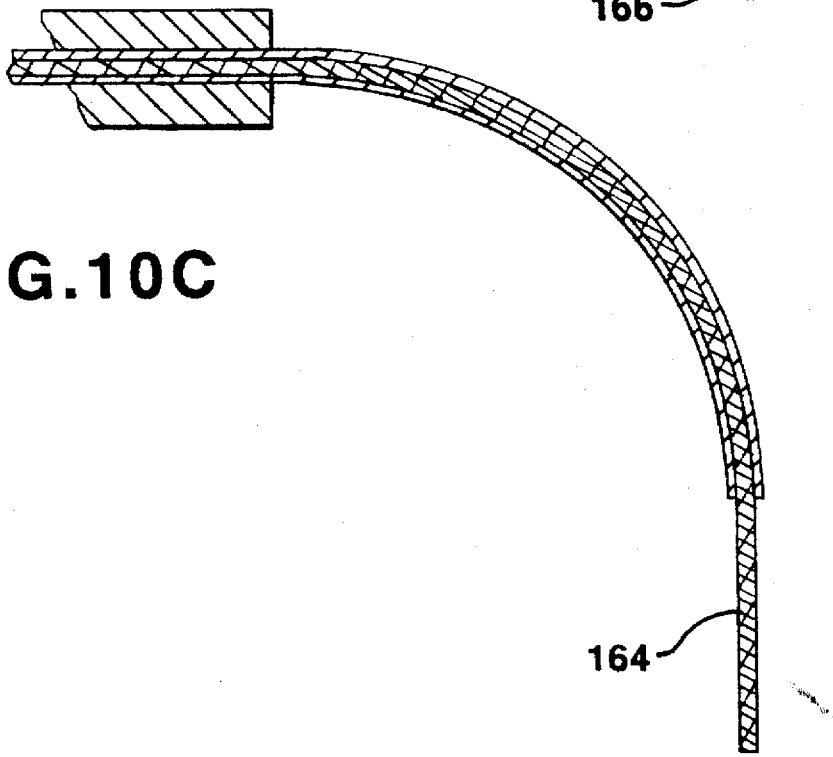
FIG.10C

FLEXIBLE CUTTING TOOL AND METHODS FOR ITS USE

FIELD OF THE INVENTION

The invention relates to flexible cutting tools and to surgical drilling and other cutting procedures using such tools.

BACKGROUND OF THE INVENTION

Modern surgical techniques often require holes or channels to be cut into bone, teeth or soft tissue, for various reasons. Holes may be drilled in bone to receive screws, sutures or bone anchors enabling anchorage of implants or reattachment of ligaments or tendons. Ordinarily, surgical drills can be employed which utilize a motor (often an air motor) and a drill bit of the desired length and diameter. However, because of the proximity of other tissue or prosthetic materials, it often becomes difficult to appropriately orient a surgical drill and drill bit so that the desired bore can be formed in tissue. Dental drills are available, of course, but have generally very short bit lengths.

U.S. Pat. No. 5,330,468 (Burkhart) proposes a drill mechanism for arthroscopic surgery in which a rotating pin of nitinol is caused to emerge from a gently bent aiming tube, drill through a thickness of bone, and then be received in an appropriately positioned receiving tube. The device itself is somewhat bulky. Another device using nitinol pins or probes is shown in U.S. Pat. No. 4,926,860 (Stice et at.). Here, a needle or other probe of nitinol may be received in a curved cannula to deliver the end of the probe to the desired location. The probe is then advanced through the cannula and exits from the cannula end in a straight orientation.

If a nitinol pin, as shown in the previously mentioned U.S. Pat. No. 5,330,468, is bent through a sharp angle and rotated at high speed, the pin becomes work hardened at the area of the bend due to its constant flexing during rotation. The superelastic characteristic of the pin in that area is reduced, and the pin can readily break. Nitinol wire drills in which a nitinol pin is rapidly rotated in a sharp bend, hence, have not become commercially successful.

SUMMARY OF THE INVENTION

We have found that an appropriate flexible cutting instrument can be formed through the use of a helically wound cable, preferably of metal and most preferably of nitinol or other superelastic alloy. Cables of this type can withstand rapid rotation while proceeding about tight bends, without substantial work hardening. Because cables are far more flexible than solid pins of the same diameter, it would be expected that the distal free end (that is, the cutting end) of a cable, since it is relatively unsupported, would tend to whip around in an uncontrolled fashion. That is, a trade-off to using a much more flexible superelastic alloy cable would be lack of control of its drilling end.

We have found that the cutting end of a flexible cable that is slidingly supported in a stationary tubular support from which the cutting end may protrude, when used as a drill, produces a bore that remains relatively straight and true as the cable is advanced, even though the cable length that protrudes from the tube is supported only by the tissue being drilled. As long as the cutting end remains in contact within the tissue being drilled, the tissue itself appears to provide sufficient support and guidance to the otherwise unsupported cutting end to keep it in a substantially straight path.

As used herein, "tissue" refers to both soft tissue and to hard tissue such as bones and teeth.

Thus, in one embodiment, the invention relates to a cutting instrument such as a drill that includes an elongated, helically wound flexible cable preferably comprising superelastic metal alloy fibers and cutting means disposed at the distal end of the cable to perform a drilling function when the cable is rotated. A motor attached to the cable remote from its distal end rotates the cable in a direction tending to tighten the helically wound fibers. That is, if the cable is given a clockwise spin, the cable should have a counterclockwise wind. Provided also is an elongated holder having an opening through which the cable may be advanced axially, the holder having a distal end for supporting the cable during a drilling operation and through which the distal end of the cable protrudes. The holder includes a cable support shaped to bend the cable through a predetermined angle adjacent its distal end and to maintain that bend as the cable is rotated and advanced in a drilling operation. In a preferred embodiment, the helically wound superelastic alloy fibers themselves are cut at the distal end so as to themselves form said cutting means. This cable is preferably so formed as to enable fibers at the distal end of the cable to separate from each other slightly under centrifugal force or axial compression or both as the cable is advanced through the holder and rotated; as a result, the diameter of the drilled hole is slightly greater than the diameter of the cable adjacent but spaced from its distal end. Axial compression of the cable end against the floor of the bore causes the individual fibers of the cable to bow outwardly and thus increase the diameter of the cable at that point.

The invention includes a method of drilling straight holes through tissue which comprises providing the drill referred to above, rotating the cable in a direction tending to tighten the helically wound fibers while continuously maintaining the cutting means at least partially within the hole being drilled and advancing the cable through the holder, whereby the wall of the hole being drilled serves to support the cutting means so that the latter advances in a substantially straight path through the tissue.

A particularly preferred procedure involves a method for fastening a hollow intramedullary rod to a bone, such as the femur, within which the rod is received. Rods of this type may be employed to internally stabilize fractures of long bones such as the femur, the tibia and the humerus. The method includes the steps of providing a drill including an elongated, flexible length of superelastic alloy bearing cutting means at its distal end and an elongated holder receivable in the hollow intramedullary rod. In this embodiment, the length of superelastic alloy preferably is in the form of a cable as described above. The holder has a distal end for supporting the length of superelastic alloy during a drilling operation and an opening through which the distal end of the length of superelastic alloy protrudes. The holder includes a support shaped to bend the length of superelastic alloy through approximately a right angle adjacent its distal end and to maintain the bend during a drilling operation. In this procedure, the holder is positioned in the intramedullary rod, the hole through which the distal end of the superelastic alloy cable length protrudes being aligned with and referencing a preformed hole in the intramedullary rod. The length of superelastic alloy is then rotated in a drilling operation and is advanced radially outwardly from the holder through the aligned holes in the holder and rod, against and through the bone and against and through the overlying muscular tissue and skin while continuously maintaining the cutting means at least partially within the hole being drilled. The point of exit of the drill from the skin is located, and a cannula is inserted over the cable to engage the hole through the bone. The cannula is stabilized with respect to the bone, the cable is retracted, and a drill is employed to enlarge the hole, the drill extending through the opposed wall of the bone. A screw fastener is inserted through the lateral hole thus drilled in the bone and through the preformed hole in the intramedullary rod to hold these elements together.

Other surgical uses of the instruments of the invention include dental procedures such as root canal surgery, the cleaning of osteolytic lesions resulting in bone cavities adjacent a prosthesis, the repair of anterior cruciate ligament damage, and the like.

DESCRIPTION OF THE DRAWINGS

FIG. 3 is a schematic, broken away diagram of a leg with a broken femur, the latter being internally stabilized by placement of an intramedullary rod; and FIG. 4 is a broken-away, schematic view of a device of the invention as the same is used in connection with the intramedullary rod shown in FIG. 3.

FIGS. 6A and 6B are broken away, cross-sectional views of a portion of the device shown in FIG. 5;

FIG. 7 is an exploded view, in partial cross-section, of a device for inserting a connector in an intramedullary rod of the type shown in FIG. 3;

FIG. 10A, FIG. 10B and FIG. 10C are broken away, cross-sectional view showing a modified embodiment of the invention; and FIG. 11 is an end view of a device of the invention of the type shown in FIGS. 10A, 10B and 10C, illustrating a modification of the device.

DETAILED DESCRIPTION

Figure 1A:
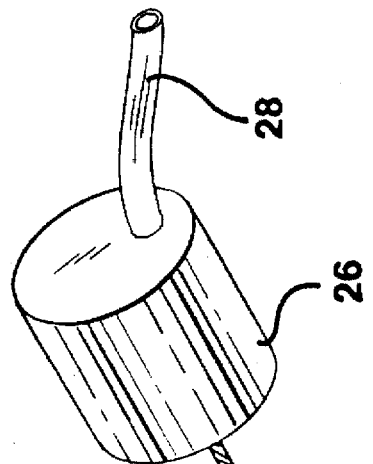
FIG. 1A is a detailed view of the distal end of the drill of FIG. 1.
Figure 1:
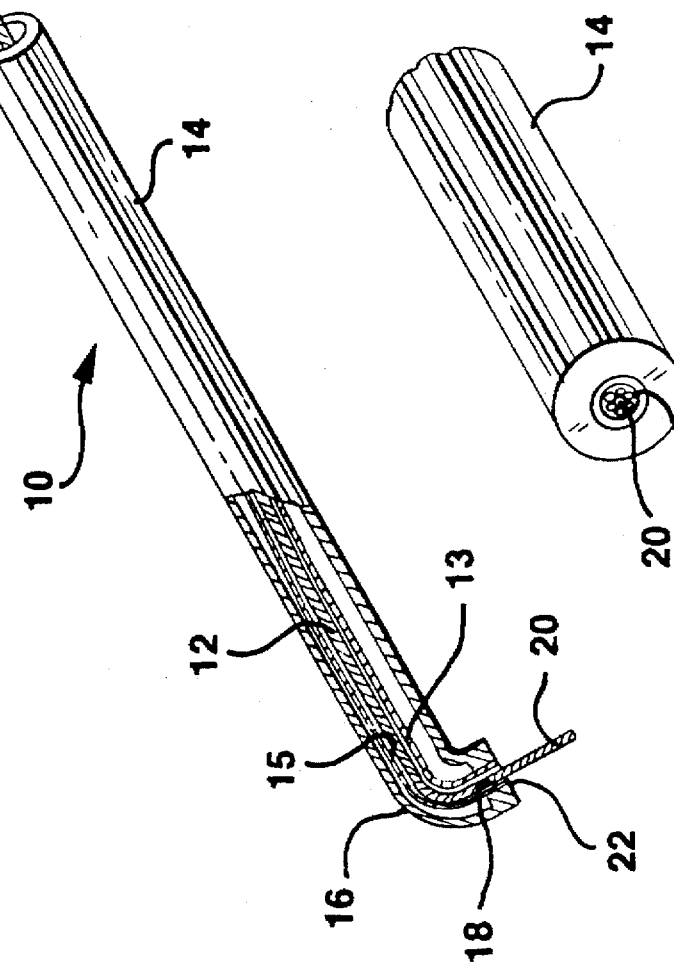
FIG. 1 is a broken-away, perspective view of a drill of the invention.

A flexible cutting tool of the invention, exemplified as a drill, is shown as 10 in FIG. 1. A flexible, helically wound cable is shown generally at 12, the cable extending through the interior of an elongated tubular support 13 that itself is supported by an elongated tubular holder 14. Support 13 closely receives the cable and supports the cable against undue lateral movement or buckling even when the cable is rotated rapidly or is under torsional or axial load. The inner diameter of the tubular support 13 preferably is no more than twice the diameter of the cable, and in general, the inner diameter of the tubular support need be only about 0.001 to 0.005 inches larger than the diameter of the cable. At its distal end 16, the tubular support 13 is bent through an angle so that its inner surface 18 serves as a supporting surface to support the cable as it bends through a predetermined angle to exit from the side of the holder 14. In FIG. 1, the cable 12 is bent through approximately 90°. Distal end 20 of the cable protrudes from the distal end 22 of the tubular support 13.

A motor 26 is shown in FIG. 1 for rotating the cable 12 about its axis. The motor can be any rotating driver, and may take the form of an electric motor or an air motor, the latter being driven by compressed air entering the motor through supply tube 28. Although the motor may be rotated at whatever speed is desired, speeds of about 50,000 rpm are appropriate. For certain uses as described in greater detail below, slower speeds are required. Rotational speeds can be varied from a few revolutions per minute up to 150,000 revolutions per minute or more. The motor 26 may be mounted to the proximal end of the cable 12 using commonly available chucking equipment, crimping techniques, or adhesive bonding. It is contemplated that the cable 12 may run through the motor 26 with the rotating portion of the motor engaging the outer walls of the cable in a manner enabling the rotating cable to be advanced axially with respect to the motor. Preferably, however, a chucking arrangement is employed in which the proximal end of the cable 12 is received in the chuck of the motor in known fashion, that is, using the chucking mechanism that is common to power drills and drill bits. With this preferred embodiment, the motor 26 is fastened to the cable 12 so that axial movement of the motor and cable distally toward the distal end of the holder will cause the end 20 of the cable to advance outwardly of the hole 22 for at least a distance equal to the depth of the desired hole. In one embodiment, the motor 26 may be mounted to the proximal end 30 of the holder, and the holder itself, rather than being formed from a single tubular member as shown in FIG. 1, may be formed of two or more tubular members that telescope together such that the length of the holder 14 can be lengthened or shortened. In this embodiment, shortening the length of the holder 14 causes the cable 12 to advance distally out of the hole 22. The telescoping portions of the handle 14 may, in fact, have mating circumferential threads such that rotation of one portion of the handle with respect to the other through a given angle will result in a predetermined advancement of the distal end 20 of the cable outwardly of the hole 22.

Figure 2:
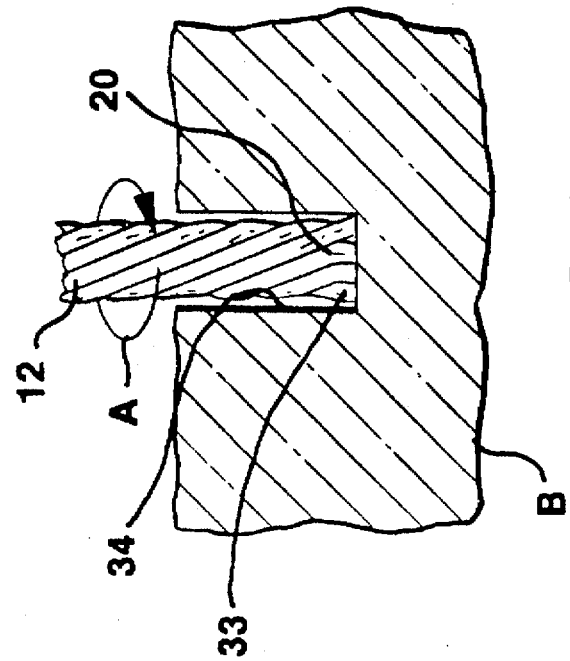
FIG. 2 is a broken-away, schematic view of a cutting tip of a drill of the invention shown forming a bore in bone.

The distal end 20 of the cable is shown best in FIG. 2. The cable, preferably of nitinol or other superelastic alloy, desirably is formed about a central core wire 32 about which are twisted a plurality of strands as shown in the drawing. Any twisted cable of the type depicted will operate, such as cables having successive layers of oppositely twisted fibers, as long as the outer layer of fibers is twisted in a direction causing the fibers to wrap more tightly as the cable is rotated. Preferably, the cable contain only a single layer of twisted fibers, the twist direction being the same for each fiber.

From FIG. 2, it will be seen that if the cable is rotated in the direction shown by the arrow A, the helically wound strands will tend to tighten upon one another, torque thus being readily transmitted from the motor to the distal end 20 of the cable. It will also be understood that if the cable is rotated by the motor 26 in the opposite direction, the cable will tend to untwist and become quite loose. Rotation in the direction of the arrow A in connection with the twist direction shown in FIG. 2 thus is important to proper operation of the drill. It should also be understood that in FIG. 2, the distal end portion of the tubular support has been omitted to enable the twisted nature of the cable to be better illustrated. In practice, the cable is supported by the tubular support throughout substantially the entire length of the cable except for the distal end portion that is received and supported in the tissue being drilled.

At its distal end, the twisted fibers forming the cable may tend to separate from one another slightly under the substantial centrifugal forces generated by the motor 26 or from axial compression of the fibers against the floor of the hole or both. FIG. 2 shows the twisted strands separating slightly as the drill is used to form a bore 34 in a bone mass B. Note that the diameter of the bore 34 is somewhat larger than the diameter of the cable 12 spaced away from the end 20 of the cable. Here, the cable strands 33 have separated and have spread outwardly slightly so that the bore 34 is slightly larger than the cable diameter. Some clearance thus is provided between the inner surface of the bore and the cable itself, and this is believed to help in preventing binding of the cable within the bore and to permit debris from the drilling operation to escape. As the rotational speed of the cable is increased, the separation of strands at the distal end of the cable increases under centrifugal force; hence, one may control the diameter of the bore through adjustment in rotational speed of the cable.

At the distal cutting edge of the twisted fibers, it should be noted that the fibers are maintained within the previous diameter of the hole and are supported by that diameter as they cut. In this manner, the hole or bore 34 itself serves as a support or guide that prevents the distal end of the cable from moving in an uncontrolled manner and which causes the bore 34 to remain straight. Soft tissue provides similar support.

The support 13 in the embodiment shown in FIG. 1 is tubular with a central lumen 15 housing the cable and being only slightly larger than the cable 12, as discussed above, so as to permit the cable to rotate substantially freely in the holder while preventing the cable as it rotates from kinking or doubling back on itself. The distal end of the holder of FIG. 1 is itself bent through a predetermined angle, exemplified as an angle of 90 degrees, the surface of the lumen at the bend furnishing the support that serves to maintain the 90 degree bend of the cable as the latter rotates and advances through the holder. Various other configurations supporting the cable at its bend can be employed. For example, the holder may simply be provided with an orifice at or adjacent its distal end through which the cable may be advanced, and the inner surface of the holder may be smoothly curved to support and maintain the bend in the cable. The holder may include an elongated groove, formed in an insert in the holder if desired, that houses and supports the cable for at least a portion of its length. If desired, the lumen 15 may be provided with constrictions spaced along its length, the constrictions providing supporting surfaces positioned to contact and support the cable at one or more points along its length.

In the drawings, the tubular support 13 and holder 14 are shown as defining a mechanically separate device which can be received within a hollow intramedullary rod or the like. In an alternative embodiment, an intramedullary rod or the like may itself define the support. For example, generally solid intramedullary rods are known in the art. Such an otherwise solid rod can be provided with art internal passage which is sized and shaped much as is the support 13 described above. In such an embodiment (not illustrated in the drawings), the intramedullary rod performs the functions of the holder 14 of the invention and the passage in the rod performs substantially the same function as the support detailed above.

Any suitable cutting tip can be used at the end of the cable 12. In one embodiment, when the cable is rotated and thus forming a bore larger than the diameter of the cable adjacent the loop. Also, if a loop cutting end is used, the loop may be used to pull a suture through the formed bore when the cable is withdrawn from the bore, thus simplifying surgical procedures involving fastening ligaments or tendons or cartilage to bone.

As noted above, the end of the cable can simply be cut straight across at a right angle to the length of the cable. The resulting sharp ends of the individual fibers thus cooperate to form the drilling tip. If desired, the fibers at the distal end of the cable may be welded together to prevent them from separating under centrifugal force. Also, a separate drill bit similar to drill bits currently in use for surgical procedures can be used, the drill bit being welded, crimped, glued or otherwise fastened to the distal end of the cable. In one embodiment, the drill bit may have cutting edges at its distal end but may include an axial bore formed in its proximal end sized to receive the distal end of the cable which can then be welded into the drill bit bore. Of course, whenever a separate drill bit is attached to the end of a cable, there is some risk that the drill bit may come loose during a drilling operation. As a result, it is preferred that the drill bit be formed by the ends of the strands forming the cable, as shown in FIG. 2.

The use of a highly flexible cable of the type described above in a drilling procedure also offers the advantage that the cable will follow, in a drilling operation, the softer part of material being cut. For example, root canal surgery commonly requires that a hole be drilled through the root of a tooth following the nerve canal. The nerve canal of a tooth is slightly curved. Dental drills currently in use are comparatively rigid and cannot, accordingly, easily follow the deviations from straightness that are common to root canals. However, the cutting tool of the present invention, which makes use of a very flexible cable, is capable of being inserted into the root canal of a tooth and, by being gently advanced, can perform the desired cleaning and nerve removal by following the normal canal curvature. Moreover, since the depth of the hole that is drilled is dependent upon the distance in which the cable is advanced through the opening in the handle, the end of the handle can be rested upon the surface of the tooth being drilled, and the depth of the bore in the tooth can be controlled with great accuracy. Further, since the fibers at the end of the cable can be caused to flare outwardly (see FIG. 2), the flared fibers can be employed in a procedure to cut, dislodge and displace material beyond the ends of the roots, a procedure that is difficult when using present day dental instruments.

The present invention provides, in a preferred embodiment, a method enabling accurate intramedullary rod placement and securement to a bone. With reference to FIG. 3, the femur F of a patient is schematically shown as having several fractures, the bone segments being internally stabilized by means of an inserted intramedullary rod 40 having a hollow interior 42 and a series of preformed holes 44, 46 formed through its walls. The purpose of these holes is to receive bone screws that are driven from the exterior of the leg inwardly through the bone wall to secure the bone to the rod.

Proper location of the holes in the intramedullary rod has been a problem. One method involves using a fluoroscope to locate the holes in the rod, and then place Stimen pins or the like percutaneously through the femur and the corresponding holes in the rod, using the pins as guides in the subsequent placement of screws. An inherent hazard of this procedure is exposure of the patient and medical staff to gamma radiation. External targeting of the rod holes without use of fluoroscopy but using instead knowledge of the hole locations with reference to the proximal (exposed) end of the rod is difficult because the rod often must bend and twist as it is impacted into the intramedullary canal of the bone. Screws that are not properly placed need to be removed and replaced, leaving an additional hole in the bone and requiring additional operating time.

According to one embodiment of the invention, this problem is approached from a different direction. Once the hollow intramedullary rod has been impacted into place in the bone, as shown in FIG. 4, a drill 50 of the invention having an appropriately slender shape is inserted into the rod from its proximal end and is advanced until the distal end 52 of the cable, bent through 90 degrees as shown in the drawing, can be extended through a hole 44 in the rod. The motor is activated and the cable is advanced axially to cause a hole to be drilled radially outwardly through the femur. The drilling operation can be continued through soft tissue exterior to the femur and can, if desired, be brought outwardly of the skin, all as is described in greater detail below in connection with FIGS. 5-7.

The invention has been described above primarily with respect to the superelastic alloy nitinol, but other superelastic materials may also be used, as well as such other materials and metals such as stainless steel. Nitinol is a superelastic (sometimes referred to as pseudoelastic) material, that is, a material that can be processed or treated to exhibit superelasticity at a desired temperature such as body temperature. A number of shape memory alloys are known to exhibit the superelastic/pseudoelastic recovery characteristic, and these are generally characterized by their ability, at room or body temperature, to be deformed from an austenitic crystal structure to a stressed-induced martensitic structure, returning to the austenitic state when the stress is removed. The alternate crystal structures give the alloy superelastic or pseudoelastic properties.

Figure 5:
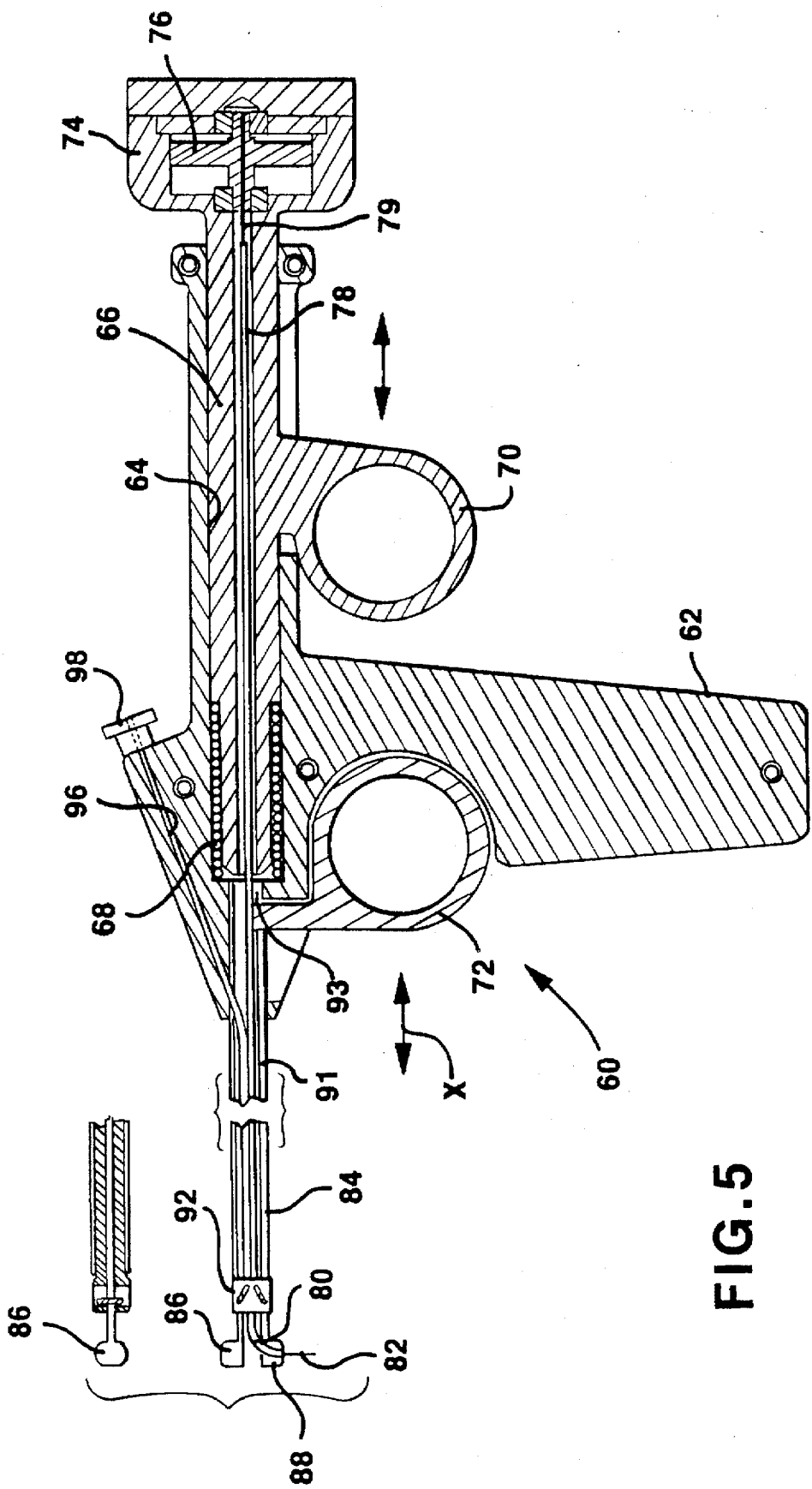
FIG. 5 is a broken away, cross-sectional view of a device similar to that of FIGS. 1 and 2, suitable for use in connection with the intramedullary rod shown in FIG. 3.

A modified device of the invention is shown in FIGS. 5 and 6 as 60. A handle grip 62 is provided with a bore 64 within which is telescopically received a tubular housing 66. An elastically compressible helical spring 68 is positioned between opposing shoulders of the handle grip and tubular housing as shown in the drawing. Finger grip 70 is provided to enable the device to be conveniently grasped in the hand such that when the finger grip 70 and handle grip 62 are squeezed towards one another, the tubular housing 66 extends more deeply into the bore 64 to cause a cable to protrude from the instrument. At its proximal end, the tubular housing has an expanded portion 74 which houses the impeller 76 of a simple air motor which is driven from an air source (not shown) and which is capable of developing substantial rotational speeds. Speeds on the order of 40,000-50,000 RPM are appropriate for many drilling functions, although speeds of rotation can be varied as desired.

Extending within the bore of the tubular housing 66 is an elongated tubular support 78 having a curved distal end 80. Extending through the tubular support is a cable 82 of the type described above sheathed throughout the majority of its length in a drive tube, the proximal end of which is axially received in and clamped in the impeller 76 as shown in the drawing. The distal end of the cable extends beyond the distal end of the drive tube and through the bend 80 of the tubular support. It will be understood that as the finger hole 70 and handle grip 62 are squeezed together, the cable 82 is caused to extend further from the curved section 80.

The handle grip 62, and its distal end, includes an elongated tube 84 terminating in opposite, outwardly extending bosses 86, 88, the bosses being so shaped as to enter the holes 44 formed in an intramedullary rod of the type shown in FIGS. 3 and 4. Boss 88 has a hole formed through it as shown best in FIG. 6B to receive the curved end 80 of the tubular support 78. The bosses 86 are formed on distally extending, generally parallel arms having upstanding pins 90 formed on them. A camming block 92 is provided with angled slots 94 within which the pins 90 are received, the slots being configured such that when the camming block is moved distally, the pins 90 and hence the bosses 86, 88 are moved together to enable the device to be removed from an intramedullary rod. On the other hand, when the cam block 92 is moved in the proximal direction, the bosses are forced away from each other and into opposing holes formed in the intramedullary rod to anchor the end of the tool appropriately in the rod. A wire 91 extends from the camming block to a finger grip 72 slidably mounted at 93 to the handle grip. As the finger grip 72 is moved toward the handle grip 70, the bosses 86, 88 are caused to separate to the position shown in FIG. 5. Movement of the finger grip 72 in the opposite direction causes the bosses to retract toward each other.

Referring again to FIG. 5, the handle grip 62 includes an oblique channel 96 for fluid delivery for lubrication, irrigation or cooling, the channel having an appropriate external fitting such as a Luer fitting 98.

With reference, then, to the procedure described above in connection with FIGS. 3 and 4, it will be understood that the tube 84 of the handle grip 62 is sufficiently long as to extend the length of an intramedullary rod. The tube 84, with the bosses held in their retracted position by the cam block 92, is inserted into the intramedullary rod until the bosses 86, 88 are adjacent to the holes 44 in the rod. Once the bosses have entered the holes (as can readily be sensed by the surgeon), the cam block 92 is moved proximally to lock the bosses in the opposing holes in the intramedullary rod. The air motor is energized, and the cable is advanced in a drilling operation as has been described earlier.

FIG. 7 depicts apparatus which can be used to place a bone screw or other connector through the bone and intramedullary rod shown in FIG. 3. As noted above, the cable 82, after drilling through the wall of the femur, will continue to drill in a substantially straight path through soft tissues of the thigh and will emerge from the skin. Shown in FIG. 7 is a hollow introducer rod 100 within which is received a cable clamp, the latter comprising a rod 102 received within a tubular housing 104. At its bottom end, the tubular housing 104 includes an internal rubber seal 108 to receive the end of the cable and to clamp onto the cable as the rod 102 is moved axially within the tube 104. The end of the cable protruding from the patient's skin is captured within the rubber seal 108 so that the cable may be firmly supported. The introducer rod 100 is then slid axially downwardly along the cable clamp and the cable while holding the cable in tension until the conical end 106 of the introducer rod is received in the rim of the hole in the femur through which the cable protrudes. The introducer rod is held firmly against the rim of the hole, and the cable clamp is then removed. The cable itself can be withdrawn from within the introducer rod, and the entire apparatus shown in FIG. 5 can be set aside. Over the introducer rod is then advanced a guide tube 110 carrying within it a drill sleeve 109. The guide tube 110 has a convenient handle 112 to aid the surgeon in supporting the instrument. At its distal end, the drill sleeve 108 has bone seating spikes 114 which are driven into the surface of the femur around the hole that had been drilled, following which the introducer rod is removed. At this point, a long surgical drill is inserted through the hollow center of the drill sleeve, and a hole of greater diameter is drilled through the femur, the drill bit passing through the intramedullary rod and thence through the opposite side of the femur. The drill and supporting drill sleeve are then removed, and a fixation screw (not shown) can be advanced through the guide tube 110 and fastened through the holes drilled in the femur and through the preformed holes in the intramedullary rod to firmly attach together the femur and the intramedullary rod.

Figure 8:
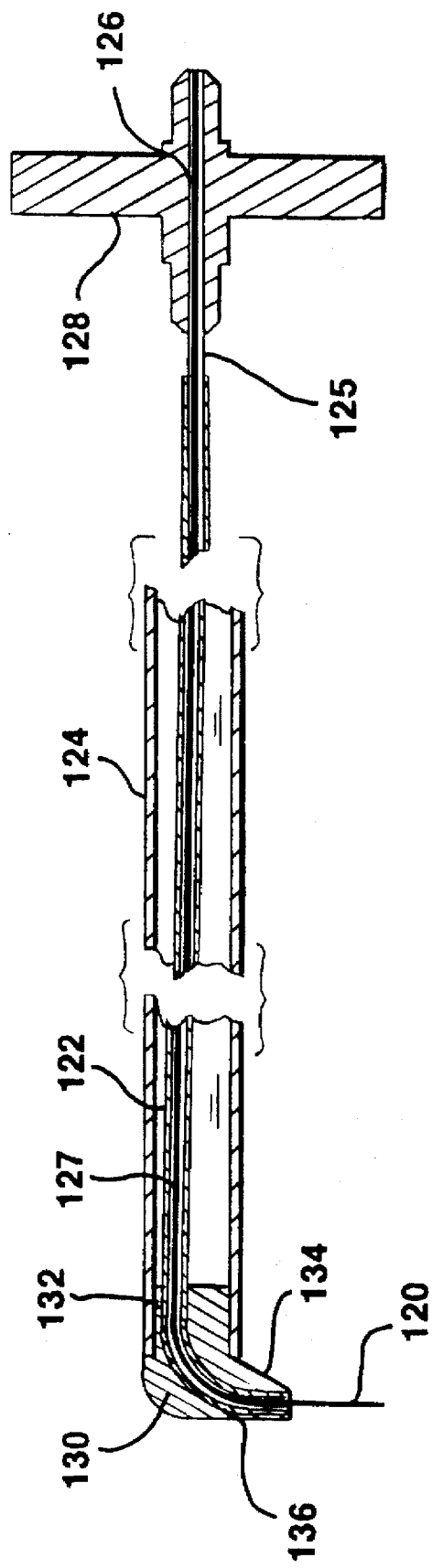
FIG. 8 is a broken away, cross-sectional view of a simplified device of the invention showing particular details.
Figure 8A:
FIG. 8A shows a specific cutting end.

FIG. 8 is a broken away, largely schematic view showing details of the distal end of a device of the invention. A length of cable as described above is shown at 120, the cable and drive tube 125 (described below) slidingly being received in a tubular support 122. The tubular support is in turn axially constrained within a tubular housing 124. As shown, the cable is sheathed in a drive tube 125 which extends from a point 127 spaced from the distal end of the cable proximally into mounting engagement with the impeller. The drive tube is secured to the cable by crimping at either or both ends, by the use of an adhesive, or by other similar means. As the air motor is moved distally, that is, to the left in FIG. 8, the cable 120 is advanced outwardly of the tubular support 122.

Note that the distal end of the tubular housing 124 includes a supporting element 130 having a proximal portion 132 that is received within the end of the tubular housing 124 and a nose 134 extending approximately at right angles to the housing 124. Supporting element 130 is formed with a curved bore within which is seated the distal end 136 of the tubular support 122, the supporting element 130 holding the tubular support 122 and distal end 136 rigidly so as to properly guide the cable 120 as it emerges from the tubular support. The nose 134 may be made as narrow and tapered as desired to enable it to fit, for example, accurately against the surface of a tooth above the root, the instrument being appropriate for use now in performing a root canal surgical procedure.

Figure 9A:
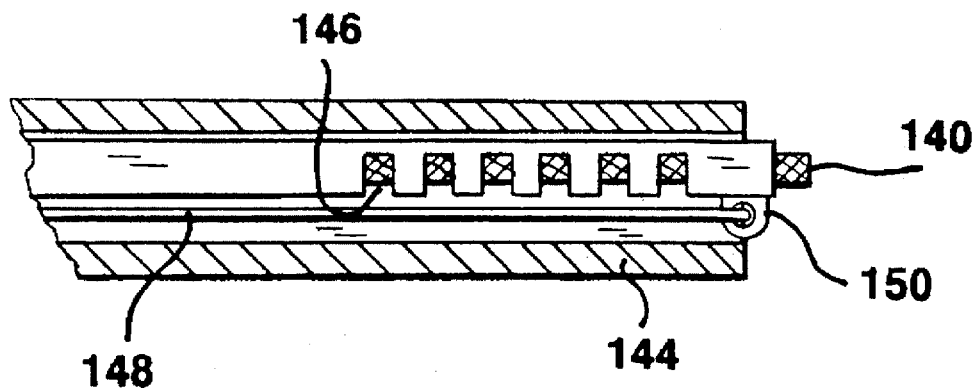
FIGS. 9A, 9B and 9C are broken away, cross-sectional views of an end portion of a device of the invention showing a method of angle adjustment.
Figure 9B:
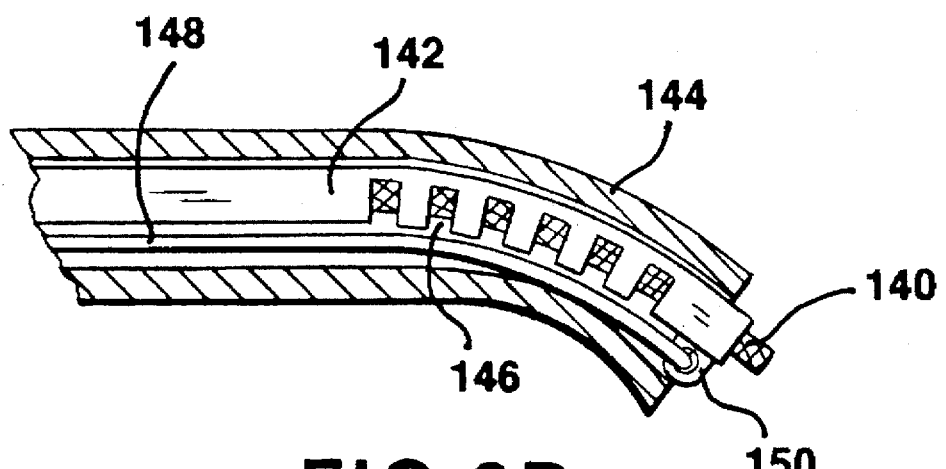
Figure 9C:
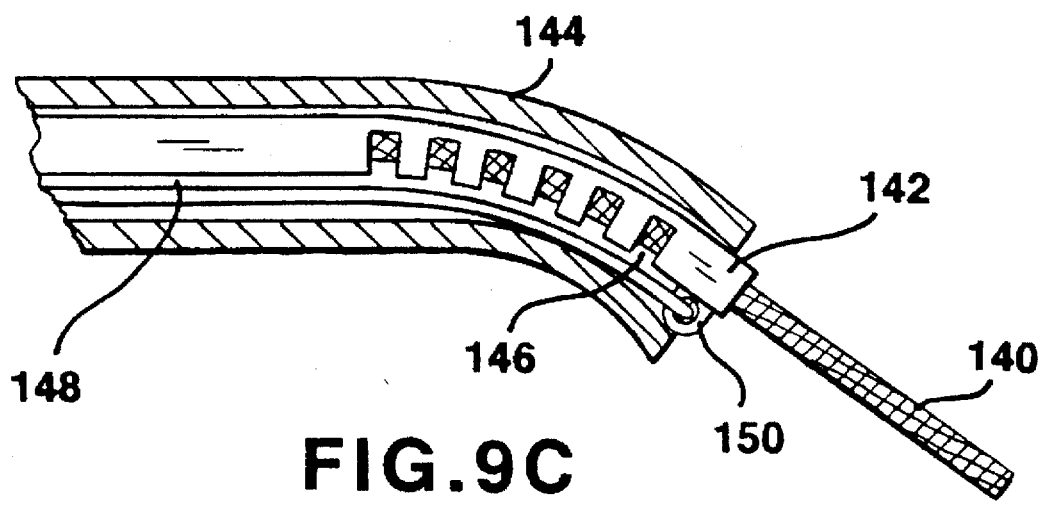

The cable may be bent adjacent to its distal end through any predetermined angle ranging from 0 degrees to 180 degrees. Moreover, the elongated tubular support holder through which the cable is passed and trained about the predetermined angle may itself be adjusted before or during use. FIGS. 9A, 9B and 9C show a cable 140 carried by tubular support 142 within an elastically bendable tubular housing 144, the latter, if desired, being made from nitinol or other superelastic alloy. The tubular support 142 is provided with a series of spaced notches 146 cut into one side wall adjacent the distal end of the support. A control wire 148 extends within the tubular housing 144 adjacent the tubular support 142, the wire being attached to the tubular support at 150 on the same side of the tubular support as are formed the notches 146. As will now be noted from FIGS. 9A, 9B and 9C, as the wire 148 is pulled proximally, the walls of the notches 146 tend to pinch together and permit the tubular support 142 to bend. This, in turn, also tends to bend the distal end of the tubular housing 144, all as illustrated in the drawing.

FIGS. 10A, 10B and 10C illustrate another way in which a predetermined angle may be set at the distal end of a device of the invention. In FIGS. 10A, 10B and 10C, an elongated tubular support holder 160 is shown emerging from a tubular housing 162. The tubular support may be bent as desired as shown in 10B, and the cable 164, which is slidably received in the tubular support 160, can then be extended from the end of the tubular support. The tubular support 160 may, if desired, be bent manually by the surgeon so as to enable the distal end 166 of the support to be appropriately placed adjacent a bone or other tissue to be drilled. Alternatively, the tubular support may be of superelastic alloy having the preformed shape shown in FIG. 10C, the flexible nature of the support 160 enabling it to be housed in a generally straight configuration within the tubular housing 162 as shown in FIG. 10A and to protrude in a curved fashion when advanced distally within the housing 162, the curved nature of the support 160 enabling it to be steered as desired.

As will be appreciated from the foregoing description, the apparatuses of the invention may be employed for a variety of purposes. One application involves anterior cruciate ligament reconstruction. In this procedure, a ligament graft, either a separate graft or a section of the patellar ligament, is passed through a hole prepared in the tibial plateau. Proper placement of the exit site of the hole in the tibial plateau is critical to long term functioning of the graft and of the knee. If the hole is placed too far anteriorly, the graft will impinge in the femoral notch, resulting in early failure. If the hole is placed too far posteriorly, the graft will not provide the needed stability to the knee.

Using conventional techniques, the distal hole in the tibia to accept the graft is drilled from an exterior anteriodistal approach. With the present invention, however, a surgeon is able to start the drilling process from within the joint space, directly targeting the desired bore location with the drill. The cable is advanced distally and emerges from the tibial anterior cortex distal to the joint. A cannulated drill is then advanced over the cable and into the joint space, exiting at the appropriate point on the tibial plateau. The same technique may be used to prepare the femoral drill hole from the intracondylar notch. Thus, by starting the drilling operation from inside the joint space, accurate location of the bore is made possible.

Osteolysis, the formation of a lesion in bone around an implant, may lead to substantial damage to the bone. Osteolytic lesions are commonly progressive, leading to loose and painful implants, fracture of supporting bones, or failure of the implant. Revision surgery is often the only available option to treat such lesions. However, the flexibility of operation that is afforded by cutting instruments of the invention may enable lesions to be cleaned and filled without extensive surgery. Once a portal is drilled through the cortical bone surrounding the lesion, a cutting instrument of the type shown in FIGS. 10A, 10B and 10C may be advanced into the lesion cavity. As the cable is advanced into the lesion, it may be carefully controlled so as to drill away small portions of the commonly much softer lesion material. However, if a substantial length of cable is permitted to protrude from the elongated cable holder tubular support, the end of the cable may be permitted to randomly tumble about the lesion cavity, selectively cleaning away the soft lesion material.

Referring now to FIG. 11, a cutting instrument of the invention, as typified in FIGS. 10A, 10B and 10C, can be equipped with various other elongated instruments for performing different functions. FIG. 11 shows the end of an instrument of the invention. Here, an outer tubular housing is shown at 170, the housing carrying within it a cable 172 and tubular cable support 174. Also carried within the housing 170 may be an optical fiber bundle 176, and small tubes 178, 180 which may be employed to flush the cutting site with water or other cleaning liquid. This construction lends itself to the cleansing of osteolytic lesions as described above. The optical fiber bundle 176 permits the position of the cable to be continuously visualized as cleaning of the cavity occurs, and the tubes 178, 180 may be employed to flush away the liberated lesion material. Particularly when the end of the cable is permitted to move randomly, the strands at the end of the cable may be unwound slightly to permit the strands to open up, or the wires of which serve to cut away the lesion material. Once the lesion is cleaned out, the lesion cavity may be filled with bone cement or with bone graft material. The use of bone graft material supports reformation of the bone in the lesion cavity, whereas bone cement would inhibit debris from infiltrating the space and triggering another osteolytic lesion. In connection with the osteolysis procedure described above, since the end of the cable may be permitted to whip about randomly in the bony cavity that is being cleaned, the speed of rotation should, of course, be far less than the speed of rotation when the instrument is being used as a drill.

While a preferred embodiment of the present invention has been described, it should be understood that various changes, adaptations and modifications may be made without departing from the spirit of the invention and the scope of the appended claims.

We claim:

1. Method for drilling a hole through animal tissue comprising providing a drill including an elongated, flexible cable comprising helically wound fibers and bearing cutting means at its distal end and an elongated holder having an opening through which the cable may be advanced axially, the holder having a distal end for supporting the cable during a drilling operation and through which the distal end of the cable protrudes, the holder including a cable support shaped to bend the cable through a predetermined angle adjacent its distal end and to maintain such bend as the cable is rotated and advanced distally, rotating said cable in a direction tending to tighten the helically wound fibers while continuously maintaining the cutting means at least partially within the hole being drilled, whereby the wall of the hole being drilled serves to support the cutting means so that the latter advances through the tissue.

2. The method of claim 1 wherein the tissue is bone.

3. The method of claim 1 wherein the tissue is soft tissue.

4. The method of claim 2 wherein said fibers are formed at the distal end of the cable so as to themselves form said cutting means, and wherein said cable is rotated so that fibers at the distal end of the cable separate from each other so as to drill a hole in said bone of a diameter larger than the diameter of the cable adjacent but spaced from its distal end.

* * * * *